US008569497B2

(12) United States Patent
Csongor et al.

(10) Patent No.: US 8,569,497 B2
(45) Date of Patent: Oct. 29, 2013

(54) PROCESS FOR THE PREPARATION OF PIPERAZINE DERIVATIVES

(75) Inventors: Eva Againe Csongor, Pomaz (HU); Laszlo Czibula, Budapest (HU); Ferenc Sebok, Mezokovacshaza (HU); Balint Juhasz, Torokbalint (HU); Janos Galambos, Budapest (HU); Katalin Nogradi, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 154 days.

(21) Appl. No.: 13/140,261

(22) PCT Filed: Dec. 18, 2009

(86) PCT No.: PCT/HU2009/000110
§ 371 (c)(1),
(2), (4) Date: Jul. 25, 2011

(87) PCT Pub. No.: WO2010/070371
PCT Pub. Date: Jun. 24, 2010

(65) Prior Publication Data
US 2011/0269959 A1 Nov. 3, 2011

(30) Foreign Application Priority Data
Dec. 18, 2008 (HU) .................................... 0800766

(51) Int. Cl.
C07D 295/135 (2006.01)
C07D 295/14 (2006.01)
(52) U.S. Cl.
USPC .......................................... 544/393; 544/121
(58) Field of Classification Search
None
See application file for complete search history.

(56) References Cited

U.S. PATENT DOCUMENTS

| | | | |
|---|---|---|---|
| 4,957,921 | A | 9/1990 | Caprathe et al. |
| 5,846,514 | A | 12/1998 | Foster et al. |
| 6,334,997 | B1 | 1/2002 | Foster et al. |
| 6,489,341 | B1 | 12/2002 | Jerussi |
| 6,528,529 | B1 | 3/2003 | Brann et al. |
| 6,566,550 | B2 | 5/2003 | Lowe, III |
| 6,919,342 | B2 | 7/2005 | Haupt |
| 7,122,576 | B2 | 10/2006 | Plata-Salaman et al. |
| 7,737,142 | B2 | 6/2010 | Csongor et al. |
| 7,829,569 | B2 | 11/2010 | Liao et al. |
| 7,875,610 | B2 | 1/2011 | Szalai et al. |
| 7,943,621 | B2 | 5/2011 | Czibula et al. |
| 7,981,897 | B2 | 7/2011 | Bathe et al. |
| 2003/0144285 | A1 | 7/2003 | Brann et al. |
| 2004/0259882 | A1 | 12/2004 | Haupt et al. |
| 2005/0107397 | A1 | 5/2005 | Galambos et al. |
| 2006/0229297 | A1 | 10/2006 | Csongor et al. |
| 2007/0259885 | A1 | 11/2007 | Bathe et al. |
| 2010/0137335 | A1 | 6/2010 | Csongor et al. |
| 2010/0197666 | A1 | 8/2010 | Laszlovsky et al. |
| 2010/0197704 | A1 | 8/2010 | Laszlovsky et al. |
| 2010/0256145 | A1 | 10/2010 | Bak-Jensen et al. |
| 2011/0059980 | A1 | 3/2011 | Oobayashi |
| 2011/0112093 | A1 | 5/2011 | Szalai et al. |
| 2011/0275804 | A1 | 11/2011 | Czibula et al. |
| 2011/0275816 | A1 | 11/2011 | Czibula et al. |

FOREIGN PATENT DOCUMENTS

| | | |
|---|---|---|
| EP | 0431580 | 3/1995 |
| HU | P03 02451 | 5/2005 |
| WO | WO 97/11070 | 3/1997 |
| WO | WO 99/50247 | 10/1999 |
| WO | WO 99/67206 | 12/1999 |
| WO | WO 01/05763 | 1/2001 |
| WO | WO 03/029233 | 4/2003 |
| WO | WO 03/064393 | 8/2003 |
| WO | WO 2005/012266 | 2/2005 |
| WO | WO 2006/082456 | 8/2006 |
| WO | WO 2007/033191 | 3/2007 |
| WO | WO 2008/139235 | 11/2008 |
| WO | WO 2008/141135 | 11/2008 |
| WO | WO 2008/142461 | 11/2008 |
| WO | WO 2010/009309 | 1/2010 |

OTHER PUBLICATIONS

Aiken, "Pramipexole in psychiatry: A systematic review of the literature," *J. Clin Psychiatry.*, 68(8):1230-1236, (2007).
Baldessarini and Tarazi, "Pharmacotherapy of Psychosis and Mania," Brunton et al. (eds.), *Goodman and Gilman's The Pharmacological Basis of Therapeutics*, 11th Edition, McGraw Hill, Chapter 18, pp. 462-500, (2005).
Belliotti, et al., "Novel cyclohexyl amides as potent and selective D3 dopamine receptor ligands," *Bioorganic & Medicinal Chemistry Letters*, 7(18):2403-2408, (1997).
Berge et al., "Pharmaceutical salts," *Journal of Pharmaceutical Sciences*, 66(1):1-19 (1977).
Bézard et al., "Attenuation of levodopa-induced dyskinesia by normalizing dopamine D3 receptor function," *Nat. Med.*, 9(6):762-767, (2003).
*Burger's Medicinal Chemistry and Drug Discovery.* vol. 1. Drug Discovery, 6th Edition. Wiley Interscience. Ed. Donald J. Abraham, ISBN 978-0-471-27090-4, Jan. 2003.
Creese et al., "Species variation in dopamine receptor binding," *Eur. J. Pharmacol.*, 60:55-46 66, (1979).
Damasio, "Alzheimer's Disease and Related Dementias," *Cecil Textbook of Medicine*, 20th Edition, vol. 2, pp. 1992-1996, (1996).

(Continued)

*Primary Examiner* — Emily Bernhardt
(74) *Attorney, Agent, or Firm* — Fish & Richardson P.C.

(57) ABSTRACT

The invention relates to a process for the preparation of the trans N-{4-{2-[4-(2,3-dichlorophenyl)-piperazine-1-yl]-ethyl}-cyclohexyl}-carbamide derivatives of general formula (I) by reacting the compound of formula (III) with a carbamoylchloride of general formula (II) which comprises carrying out the reaction in a mixture of a solvent and concentrated aqueous solution of an alkali hydroxide at a temperature between 40-100° C. in the presence of a phase transfer catalyst, separating the phases and washing the organic layer then removing the solvent and drying the compound of formula (I) obtained until its weight is constant.

7 Claims, No Drawings

(56) References Cited

OTHER PUBLICATIONS

Dean [Editor]. "Recent Advances in the Synthesis and Applications of Radiolabeled Compounds for Drug Discovery and Development," *Curr., Pharm. Des.*, vol. 6, No. 10, [Table of Contents] CAN 133:68895 AN 2000:473538 CAPLUS; 3 pages, (2000).
Di Chiara, "Drug addiction as dopamine-dependent associative learning disorder," *Eur. J. Pharmacol.*, 375:13-30, (1999).
Eli Lilly and Company, "Zyprexa Olanzapine Tablets . . ." MedWatch Safety Alerts for Human Medical Products, FDA [online]. Retrieved rom the Internet< URL: http://www.fda.gov/medwatch/safety/2006/Aug_Pls/Zyprexa_PI.pdf>, 31 pages, (2004).
Evans, "Synthesis of radiolabeled compounds," *J. Radioanal. Chem.*, 64(1-2):9-32, (1981).
Glase et al., "4-bromo-1-methoxy-N-[2-(4-aryl-1-piperazinyl)ethyl]-2-naphthalenecarboxamides: Selective dopamine D3 receptor partial agonists," *Bioorganic & Medicinal Chemistry Letters*, 6(12):1361-1366, (1996).
Goodwin and Jamison, In: *Manic-depressive illness*, New York: Oxford University Press, pp. 642-647, (1990).
Greengrass and Bremner, "Binding characteristics of 3H-prazosin to rat brain alpha-adrenergic receptors," *Eur. J. Pharmacol.*, 55(3):323-326, (1979).
Guérémy et al., "2-Amino-6-chloro-4-(N-methylpiperazino) pyrimidines, inhibitors of spiroperidol binding," *J. Med. Chem.*, 25(12):1459-1465, (1982).
Gurevich and Joyce, "Distribution of dopamine D3 receptor expressing neurons in the human forebrain: comparison with D2 receptor expressing neurons," *Neuropsychopharmacology*, 1999, 20:60-80.
Gurevich et al., "Mesolimbic dopamine D3 receptors and use of antipsychotics in patients with schizophrenia. A postmortem study." *Arch Gen Psychiatry.*, 54(3):225-232, (1997).
Guy, *ECDEU Assessment Manual for Psychopharmacology*. Rockville, Md: US Department of Health, Education, and Welfare, pp. 218-222, Publication ADM 76-338, (1976).
Gyertyan and Saghy, "Effects of dopamine $D_3$ receptor antagonists on spontaneous and agonist-reduced motor activity in NMRI mice and Wistar rats: comparative study with nafadotride, U 99194A and SB 277011," *Behavioural Pharmacology*, 15(4):253-262, (2004).
Gyertyán and Sághy, "The selective dopamine D3 receptor antagonists, SB 277011-A and S 33084 block haloperidol-induced catalepsy in rats," *Eur. J. Pharmacol.*, 572:171-174, (2007).
Gyertyán et al., "Subnanomolar dopamine D3 receptor antagonism coupled to moderate D2 affinity results in favourable antipsychotic-like activity: Behavioral Data," [abstract]. *Int. J. Neuropsychopharmacol.*, 5 Suppl. 1:174, 2002.
Heidbreder et al., "The role of central dopamine D3 receptors in drug addiction: a review of pharmacological evidence," *Brain Res. Rev.*, 49:77-105, (2005).
Janssen, "Risperdal Consta (risperidone) Long-Acting Injection," MedWatch Safety Alerts for Human Medical Products, FDA [online] Retrieved from the Internet< URL: http://www.fda.gov/medwatch/safety/2006/Sep_Pis/RisperdalConsta_Pl.pdf>, 39 pages (2006).
Joyce, "Dopamine D3 receptor as a therapeutic target for antipsychotic and antiparkinsonian drugs," Pharmacol. Therap., 90:231-259, (2001).
Kabalka and Varma, "The synthesis of radiolabeled compounds via organometallic intermediates," *Tetrahedron*, 45(21):6601-6621, (1989).
Kay et al., "The positive and negative syndrome scale (PANSS) for schizophrenia," *Schizophr. Bull.*, 13:261-276, (1987).
Keck, "The management of acute mania," *British Medical Journal*, 327(7422):1002-1003, (2003).
King et al. (Oral solid dosage forms, in Remington's Pharmaceutical Sceicnes; Gennaro, A., Ed., 17th Edition, Mack Publishing Company, Easton PA, Chapter 90, pp. 1603-1632.
Laszy et al., "Dopamine D3 receptor antagonists improve the learning performance in memory impaired rats," *Psychopharmacol.*, 179(3):567-575, (2005).

Layzer, Degenerative Diseases of the Nervous System, *Cecil Textbook of Medicine*, 20th Edition, vol. 2, pp. 2050-2057, (1996).
Le Foll et al., "Dopamine D3 receptor ligands for the treatment of tobacco dependence," *Expert Opin Investig Drugs*, 16(1):45-57, (2007).
Lehman et al., "Practice guideline for the treatment of patients with schizophrenia, second edition," *Am. J. Psychiatry*, 161(2 Suppl):1-56, (2004).
Levant and McCarson, "D(3) dopamine receptors in rat spinal cord: implications for sensory and motor function," *Neurosci. Lett.*, 303:9-12 (2001).
Levant et al., "Dopamine $D_3$ receptor: relevance for the drug treatment of Parkinson's disease," *CNS Drugs*, 12:391-402, (1999).
Levant, "The D3 dopamine receptor: neurobiology and potential clinical relevance," *Pharmacol. Rev.*, 49(3):231-252, (1997).
Maj et al., "Effect of antidepressant drugs administered repeatedly on the dopamine D3 receptors in the rat brain," *Eur. J. Pharmacol.* 351:31-37, (1998).
Millan et al., "S33084, a novel, potent, selective, and competitive antagonist at dopamine D(3)-receptors: II. Functional and behavioral profile compared with GR218,231 and L741,626," *J. Pharmacol. Exp. Ther.*, 2000, 293:1063-1073.
Millan et al., "The dopamine D3 receptor antagonist, (+)-S 14297, blocks the cataleptic properties of haloperidol in rats," *Eur. J. Pharmacol.*, 321:R7-R9, (1997).
Montgomery and Asberg, "A new depression scale designed to be sensitive to change," *Br. J. Psychiatry*, 134:382-389, (1979).
Mueser and McGurk, "Schizophrenia," *Lancet*, 363:2063-2072, (2004).
Müller-Oerlinghausen et al., "Bipolar disorder," *Lancet*, 359(9302):241-247, (2002).
Nassar et al., "Improving the decision-making process in structural modification of drug candidates: reducing toxicity," *Drug Discov Today*, 9(24):1055-1064, (2004).
Nyberg et al., "Positron emission tomography of in-vivo binding characteristics of atypical antipsychotic drugs. Review of D2 and 5-HT2 receptor occupancy studies and clinical response," *Br. J. Psychiatry. Suppl.*, 29:40-44, (1996).
Pacher and Kecskeméti, "Cardiovascular side effects of new antidepressants and antipsychotics: new drugs, old concerns?" *Curr. Pharm. Des.*, 10(20):2463-2475, (2004).
Papp and Wieronska, "Antidepressant-like activity of amisulpride in two animal models of depression," *J. Psychopharmacol.*, 14:46-52, (2000).
Pilla et al., "Selective inhibition of cocaine-seeking behaviour by a partial dopamine D3 receptor agonist," *Nature*, 400:371-375, (1999).
Reavill et al., "Pharmacological actions of a novel, high-affinity, and selective human dopamine D(3) receptor antagonist, SB-277011-A," *A. J. Pharmacol. Exp. Ther.*, 294:1154-1165, (2000).
Rogóz et al., "Anxiolytic-like effect of nafadotride and PNU 99194A, dopamine D3 receptor antagonists in animal models," *Pol J Pharmacol.*, 52(6):459-462, (2000).
Russell, "Neurobiology of animal models of attention-deficit hyperactivity disorder," *J. Neurosci. Methods* 161:185-198, (2007).
Sachs, "Unmet clinical needs in bipolar disorder," J. Clin. Psychopharmacol., 23(3 Suppl 1):S2-S8, (2003).
Sautel et al., "Nafadotride, a potent preferential dopamine D3 receptor antagonist, activates locomotion in rodents," *J. Pharmacol. Exp. Ther.*, 1995, 275:1239-1246.
Schwartz et al., "Dopamine D3 receptor: basic and clinical aspects," *Clin Neuropharmacol.*, 16(4):295-314, (1993).
Schwartz et. al., "Possible implications of the dopamine D(3) receptor in schizophrenia and in antipsychotic drug actions," *Brain Res. Rev.*, 31(2-3):277-287, (2000).
Seeman, "Antipsychotic drugs, dopamine receptors and schizophrenia," *Clin. Neurosci. Res.*, 1:53-60, (2001).
Seeman, "Brain dopamine receptors" *Pharmacological Reviews*, 32(3): 229-313 (1980).
Shafer and Levant, "The D3 dopamine receptor in cellular and organismal function," *Psychopharmacology* (Berl), v, 135:1-16, 1998.
Shalev et al., "Neurobiology of relapse to heroin and cocaine seeking: a review.," *Pharmacol. Rev.* 54 (1), 1-42, (2002).

(56) References Cited

OTHER PUBLICATIONS

Sigala et al., "Opposite effects of dopamine $D_2$ and $D_3$ receptors on learning and memory in the rat," *Eur. J. Pharmacol.*, 336:107-112, (1997).

Smith et al., "The dopamine D3/D2 receptor agonist 7-OH-DPAT induces cognitive impairment in the marmoset," *Pharmacol. Biochem. Behav.*, 63:201-211, (1999).

Sokoloff et al., "Molecular cloning and characterization of a novel dopamine receptor (D3) as a target for neuroleptics," *Nature*, 347:146-151, (1990).

Souillac, et al., Characterization of Delivery Systems, Differential Scanning Calorimetry, pp. 217-218 (in Encyclopedia of Controlled Drug Delivery, 1999, John Wiley & Sons, pp. 212-227), (1999).

Stahl and Grady, "A critical review of atypical antipsychotic utilization: comparing monotherapy with polypharmacy and augmentation," *Curr. Med. Chem.*, 11:313-327, (2004).

Stahl, *Essential Psychopharmacology: Neuroscientific Basis and Practical Applications*, 2nd ed., p. 409, Cambridge University Press, pp. 409-414, (2000).

Steiner et al., "D3 dopamine receptor-deficient mouse: evidence for reduced anxiety," *Physiol Behav.*, 63(1):137-141, (1997).

Stemp et al., "Design and synthesis of trans-N-[4-[2-(6-cyano-1,2,3,4-tetrahydroisoquinolin-2-yl)ethyl]cyclohexyl]-4-quinolinecarboxamide (SB-277011): A potent and selective dopamine D(3) receptor antagonist with high oral bioavailability and CNS penetration in the rat," *J. Med. Chem.*, 43(9):1878-1885, (2000).

Tada et al., "Combined treatment of quetiapine with haloperidol in animal models of antipsychotic effect and extrapyramidal side effects: comparison with risperidone and chlorpromazine," *Psychopharmacology (Berl)*, 176(1):94-100, (2004).

Thanos et al., "The effects of two highly selective dopamine D3 receptor antagonists (SB-277011A and NGB-2904) on food self-administration in a rodent model of obesity," *Pharmacol Biochem Behav.* 89: 499-507, (2008).

Ukai et al., "Effects of the dopamine D3 receptor agonist, R(+)-7-hydroxy-N,N-di-n-propyl-2-aminotetralin, on memory processes in mice," *Eur. J. Pharmacol.*, 324:147-151, (1997).

Ulrich, Chapter 4: Crystallization, *Kirk-Othmer Encyclopedia of Chemical Technology*, 7 pages, (2002).

van der Kooij and Glennon, "Animal models concerning the role of dopamine in attention-deficit hyperactivity disorder," *Neuroscience and Biobehavioral Reviews*, 31: 597-618, (2007).

Waters et al., "Differential effects of dopamine D2 and D3 receptor antagonists in regard to dopamine release, in vivo receptor displacement and behavior," *J. Neural Transm. Gen. Sect.*, 98:39-55, (1994).

West, *Solid State Chemistry and Its Applications*, Wiley, pp. 358, (1988).

Willner et al., "Dopaminergic mechanism of antidepressant action in depressed patients," *J. Affective Disorders* 86: 37-45, (2005).

Wong and Van Tol, "Schizophrenia: from phenomenology to neurobiology," *Neurosci. Biobehav. Rev.*, 27(3):269-306, (2003).

World Health Organization, World Health Report 2001, "Mental Health: New Understanding, New Hope." http://www.who.int/whr/2001/en/2001, (2001).

Wyatt and Henter, "An economic evaluation of manic-depressive illness—1991," *Soc. Psychiatry Psychiatr. Epidemiol.*, 30(5):213-219, (1995).

Youdim, "The path from anti Parkinson drug selegiline and rasagiline to multifunctional neuroprotective anti Alzheimer drugs ladostigil and m30," *Curr Alzheimer Res.*, 3(5):541-550, 2006.

Young, et al., "A rating scale for mania: reliability, validity and sensitivity," *The British Journal of Psychiatry*, 133:429-435, (1978).

Zink et al., "Combination of amisulpride and olanzapine in treatment-resistant schizophrenic psychoses," *Eur. Psychiatry*, 19:56-58, (2004).

International Search Report for PCT/HU2009/00110, mailed Mar. 11, 2010, 2 pages.

International Preliminary Report on Patentability and Written Opinion for PCT/HU2009/000110, issued Jun. 21, 2011, 6 pages.

EP Search Report dated Mar. 3, 2010, mailed Mar. 11, 2010, Authorized Officer Marc Gettins.

Han; Advances in Characterization of Pharmaceutical Hydrates; Trends in Bio/Pharmaceutical Industry; 2006; 2(3):25-29.

Vippagunta et al; Crystalline Solids; Advanced Drug Delivery Reviews; 2001; 48(1):3-26.

Morissette et al; High-throughput crystallization: polymorphs, salts, co-crystals and solvates of pharmaceutical solids; Adv Drug Deliv Rev; Feb. 2004; 56(3):275-300.

Nassar et al; Improving the decision-making process in structural modification of drug candidates: reducing toxicity; Drug Discov Today; Dec. 2004; 9(24):1055-1064.

Nassar et al; Improving the decision-making process in the structural modification of drug candidates: enhancing metabolic stability; Drug Discov Today; Dec. 2004; 9(23):1020-1028.

Pacher and Kecskeméti; Cardiovascular side effects of new antidepressants and antipsychotics: new drugs, old concerns?; Curr. Pharm. Des.; 2004; 10(20):2463-2475.

PROCESS FOR THE PREPARATION OF PIPERAZINE DERIVATIVES

CROSS-REFERENCE TO RELATED APPLICATIONS

This application is a National Stage application under 35 U.S.C. §371 of International Application No. PCT/HU2009/000110, having an International Filing Date of Dec. 18, 2009, which claims the benefit of priority of HU Application No. P08 00766, having a filing date of Dec. 18, 2008, all of which are incorporated herein in their entirety.

FIELD OF THE INVENTION

The present invention relates to a new process for the preparation of trans-N-{4-{2-[4-(2,3-dichlorophenyl)-piperazine-1-il]-ethyl}-cyclohexyl}-carbamid derivatives of general formula (I).

BACKGROUND ART

Compounds of general formula (I) were originally disclosed in the Hungarian Patent Specification No. P0302451 as D3/D2 receptor antagonists. In the P0302451 specification three reaction routes (A, B, C methods) are given for the preparation of compounds of formula (I). According to method "A" an amine derivative is reacted with a (tio)carbamoylchloride compound. In Example 3, Method A of P0302451 the amine is reacted with N,N-dimethyl-carbamoylchloride in anhydrous condition in the presence of triethylamine.

From the industrial point of view drawbacks of the above "A" procedure are the long reaction time (48 hours) and poor yield (65%). Besides, the end product obtained should be purified in an additional recrystallization step.

Our aim was to provide a process lacking the disadvantages of the previous process, i.e. to prepare compounds of formula (I) by an easy-to-working up manner with a shorter reaction time and better yield.

BRIEF DESCRIPTION OF THE INVENTION

In the course of our experiments we have surprisingly found that when the compound of formula (III)

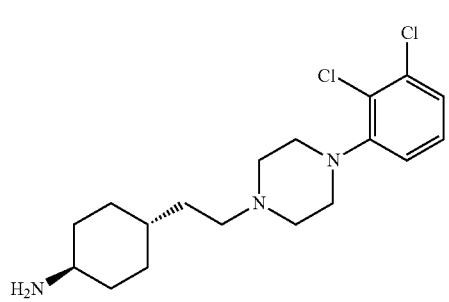

or a salt and/or a hydrate and/or a solvate thereof is reacted with a carbamoylchloride of general formula (II)

wherein $R_1$ and $R_2$ represent independently $C_{1-6}$ alkyl with straight or branched chain optionally substituted with aryl group, or $C_{2-7}$ alkenyl group containing 1-3 double bonds, or monocyclic, bicyclic or tricyclic aryl group optionally substituted with one or more $C_{1-6}$ alkoxy, trifluoro-C1-6 alkoxy, C1-6 alkoxycarbonyl, C1-6 alkanoyl, aryl, C1-6 alkyltio, halogen or cyano groups, or optionally substituted monocyclic, bicyclic or tricyclic cycloalkyl group, or $R_1$ and $R_2$ together with the adjacent nitrogen atom may form an optionally substituted, saturated or unsaturated, monocyclic or bicyclic heterocyclic ring which may contain further heteroatoms selected from oxygen, nitrogen or sulphur atoms in the mixture of a solvent and a concentrated aqueous basic solution in the presence of a tetra alkyl-ammonium salt as phase transfer catalyst a compound of general formula (I)

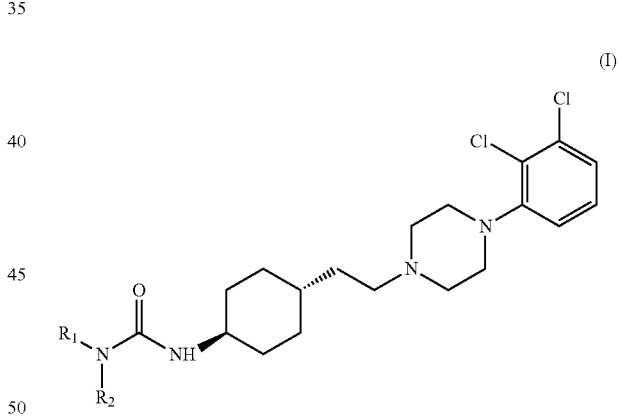

wherein $R_1$ and $R_2$ are as described above—is obtained with high yield (above 90%) and short reaction time.

Applying the process according to the invention the working-up process becomes easier: the organic and aqueous phases are separated then after aqueous washing of the organic phase the solvent is removed by distillation and the end product is obtained.

DETAILED DESCRIPTION OF THE INVENTION

The invention relates to a new process for the preparation of compounds of general formula (I)

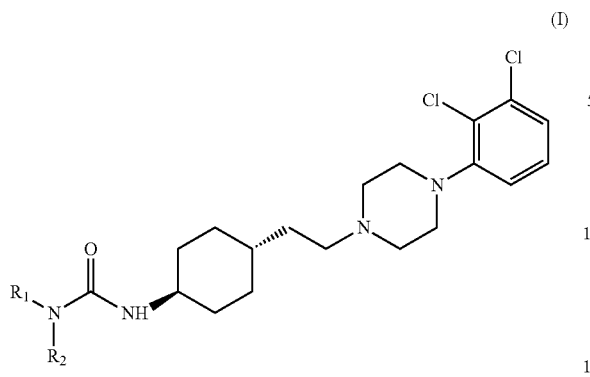

(I)

wherein

R₁ and R₂ represent independently

C$_{1-6}$ alkyl with straight or branched chain optionally substituted with aryl group, or C$_{2-7}$ alkenyl group containing 1-3 double bonds, or monocyclic, bicyclic or tricyclic aryl group optionally substituted with one or more C$_{1-6}$ alkoxy, trifluoro-C1-6 alkoxy, C1-6 alkoxycarbonyl, C1-6 alkanoyl, aryl, C1-6 alkyltio, halogen or cyano groups, or optionally substituted monocyclic, bicyclic or tricyclic cycloalkyl group, or R₁ and R₂ together with the adjacent nitrogen atom may form an optionally substituted, saturated or unsaturated, monocyclic or bicyclic heterocyclic ring which may contain further heteroatoms selected from oxygen, nitrogen or sulphur atoms.

The advantages of the invention are that the reaction time becomes shorter and the end product can be recovered from the reaction mixture in high purity without further purification, wherein the yield is over 90%.

When R₁ and R₂ represent aryl, the aryl moiety may be a group selected from phenyl, tolyl, naphthyl and phenanthryl groups.

In the procedure according to the invention the compound of formula (III)

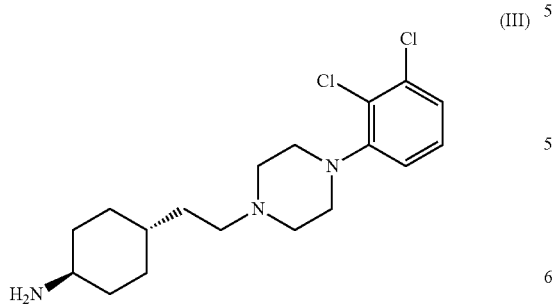

(III)

or a salt and/or a hydrate and/or a solvate thereof is reacted with a carbamoylchloride of general formula (II)

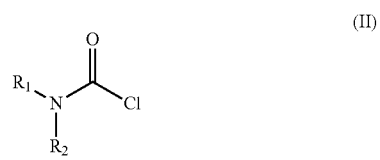

(II)

wherein R₁ and R₂ are described above, in the mixture of a solvent and a concentrated basic solution in the presence of a phase transfer catalyst. In this manner the end product is obtained with shorter reaction time (9-10 hours) and good yield (above 90%).

In a preferred embodiment of the invention the concentrated base is an aqueous solution of an alkali hydroxide, for example NaOH or KOH.

The phase transfer catalyst is a tetraalkylammonium salt, wherein the alkyl moiety may have a C1-6 straight or branched chain. In the choice of a suitable phase transfer catalyst the easy handling can be an important factor. Preferred phase transfer catalysts are the tetra-n-butyl ammonium salts or tetramethylammonium salts, wherein the salt forming anion may be sulphate, chloride or bromide anion.

Suitable solvents, which can be used in the process according to the invention include neutral water immiscible solvents, for example toluene, dichloromethane, chlorobenzene or xylene. In a preferred embodiment of the invention preferably dichloromethane can be used as solvent.

In the working-up step of the process according to the invention the organic and aqueous phases are separated, then after aqueous washing of the organic phase the solvent is removed by distillation and the desired end product is obtained.

EXAMPLES

The invention is further illustrated by the following non-limiting Examples.

Example 1

Preparation of trans 4-{2-[4-(2,3-dichlorophenyl)-piperazine-1-yl]-ethyl}-N,N-dimethylcarbamoyl-cyclohexylamine Into a 500 ml four-necked flask 180 ml of dichloromethane, 40 ml of 40% sodium hydroxide, 0.54 g (0.002 mol) of tetra-n-butylammonium bromide and 3.12 g (0.029 mol) of N,N-dimethylcarbamoylchloride are added. The mixture is stirred at a temperature between 20-25° C. for 30 minutes then 6.24 g (0.0145 mol) of trans 4-{2-[4-(2,3-dichlorophenyl)-piperazine-1-yl]-ethyl}-cyclohexyl amine dihydrochloride is added. With rigorous stirring the reaction mixture is placed into an oil bath preheated to 45-50° C. and heated to boiling temperature under nitrogen for 10 hours. Then the reaction mixture is cooled to room temperature, the phases are separated and the organic layer is washed with 3×80 ml of water and then 80 ml of 10% sodium chloride solution. The solvent is removed under vacuum; the residue obtained is further dried at maximum 50° C. temperature, until its weight is constant.

Dry weight: 5.7 g (92%).

Melting point: 212-214° C.

Example 2

Preparation of trans 4-{2-[4-(2,3-dichlorophenyl)-piperazine-1-yl]-ethyl}-N,N-dimethylcarbamoyl-cyclohexylamine Into a 500 ml four-necked flask 180 ml of dichloromethane, 40 ml of 40% sodium hydroxide, 0.54 g (0.002 mol) of tetra-n-butylammonium bromide and 3.12 g (0.029 mol) of N,N-dimethylcarbamoyl chloride are added. The mixture is stirred at a temperature between 20-25° C. for 30 minutes then 6.50 g (0.0145 mol) of trans 4-{2-[4-(2,3-dichlorophenyl)-piperazine-1-yl]-ethyl}-cyclohexyl amine dihydrochloride monohydrate is added. With rigorous stirring the reaction mixture is placed into an oil bath preheated to 45-50° C. and heated to boiling temperature under nitrogen for 10 hours. Then the reaction mixture is cooled to room temperature, the phases are separated and the organic layer is washed with 3×80 ml of water and then 80 ml of 10% sodium chloride solution. The solvent is removed under vacuum; the residue obtained is further dried at maximum 50° C. temperature, until its weight is constant.

Dry weight: 5.7 g (92%).

Melting point: 212-214° C.

Example 3

Preparation of trans N-{4-{2-[4-(2,3-dichlorophenyl)-piperazine-1-yl]-ethyl}-cyclohexyl}-morpholine-4-carbonic acid amide Into a 500 ml four-necked flask 400 ml of dichloromethane, 40 ml of 40% sodium hydroxide, 1.2 g (0.0036 mol) of tetra-n-butylammonium bromide and 11 g (0.074 mol) of N,N-dimethyl carbamoyl chloride are added. The mixture is stirred at a temperature between 20-25° C. for 30 minutes then 15.5 g (0.036 mol) of trans 4-{2-[4-(2,3-dichlorophenyl)-piperazine-1-yl]-ethyl}-cyclohexyl amine dihydrochloride is added. With rigorous stirring the reaction mixture is placed into an oil bath preheated to 45-50° C. and heated to boiling temperature under nitrogen for 4 hours. Then the reaction mixture is cooled to room temperature, the phases are separated and the organic layer is washed with 3×80 ml of water and then 150 ml of 10% sodium chloride solution. The solvent is removed under vacuum; the residue obtained is further dried at maximum 50° C. temperature, until its weight is constant.

Dry weight: 15.2 g (90%).

Melting point: 203-205° C.

The invention claimed is:

1. A process for the preparation of a compound of general formula (I)

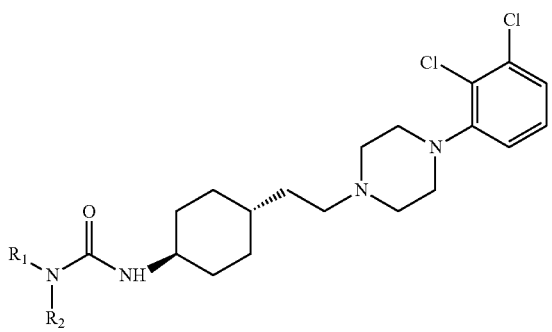

wherein
$R_1$ and $R_2$ represent independently
$C_{1-6}$ alkyl with straight or branched chain optionally substituted with aryl group, or
$C_{2-7}$ alkenyl group containing 1-3 double bonds, or
monocyclic, bicyclic or tricyclic aryl group optionally substituted with one or more $C_{1-6}$ alkoxy, trifluoro-C1-6 alkoxy, C1-6 alkoxycarbonyl, C1-6 alkanoyl, aryl, C1-6 alkylthio, halogen or cyano groups, or
a monocyclic, bicyclic or tricyclic cycloalkyl group, or
$R_1$ and $R_2$ together with the adjacent nitrogen atom may form a saturated or unsaturated, monocyclic or bicyclic heterocyclic ring which may contain further heteroatoms selected from oxygen, nitrogen or sulphur atoms comprising reacting the compound of formula (III)

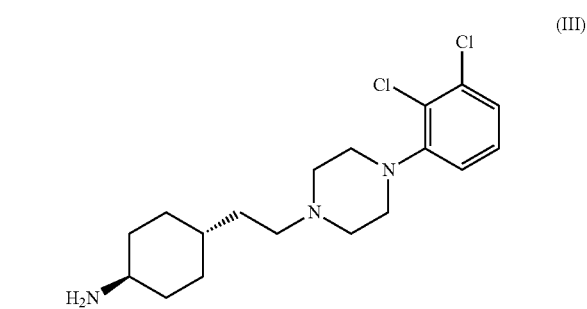 [SMILES: N[C@H]1CC[C@H](CCN2CCN(c3cccc(Cl)c3Cl)CC2)CC1]

with a carbamoylchloride of general formula (II)

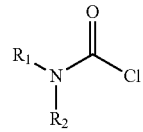

wherein $R_1$ and $R_2$ are as described above which comprises carrying out the reaction in a mixture of a solvent and concentrated aqueous solution of an alkali hydroxide at a temperature between 40-100° C. in the presence of a phase transfer catalyst, separating the phases and washing the organic layer then removing the solvent and drying the compound of formula (I) obtained until its weight is constant.

2. A process according to claim 1 characterized in that the phase transfer catalyst is a tetra alkyl ammonium salt.

3. A process according to claim 2 characterized in that the tetra alkyl ammonium salt is a tetra n-butyl ammonium halogenide.

4. A process according to claim 3 characterized in that the tetra alkyl ammonium salt is tetra alkyl ammonium bromide.

5. A process according to claim 1 characterized in that the solvent is an inert water immiscible solvent.

6. A process according to claim 1 characterized in that the solvent is toluene, dichloromethane, chlorobenzene or xylene.

7. A process according to claim 1 characterized in that the reaction is carried out at a temperature between 45 -50° C.

* * * * *

UNITED STATES PATENT AND TRADEMARK OFFICE
CERTIFICATE OF CORRECTION

| | | |
|---|---|---|
| PATENT NO. | : 8,569,497 B2 | Page 1 of 1 |
| APPLICATION NO. | : 13/140261 | |
| DATED | : October 29, 2013 | |
| INVENTOR(S) | : Csongor et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 193 days.

Signed and Sealed this
Fourteenth Day of April, 2015

Michelle K. Lee
*Director of the United States Patent and Trademark Office*